(12) United States Patent
Medina et al.

(10) Patent No.: US 8,532,729 B2
(45) Date of Patent: Sep. 10, 2013

(54) MOLDABLE EAR SENSOR

(75) Inventors: Casey V. Medina, Westminster, CO (US); Paul Von Der Lippe, Loveland, CO (US); Charles Haisley, Boulder, CO (US); David P. Besko, Thornton, CO (US); John Battista, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 194 days.

(21) Appl. No.: 13/077,319

(22) Filed: Mar. 31, 2011

(65) Prior Publication Data

US 2012/0253159 A1    Oct. 4, 2012

(51) Int. Cl.
*A61B 5/1455* (2006.01)

(52) U.S. Cl.
USPC ............ 600/344; 600/322; 600/323; 600/310

(58) Field of Classification Search
USPC .................................................. 600/309–344
See application file for complete search history.

(56) References Cited

U.S. PATENT DOCUMENTS

| | | | |
|---|---|---|---|
| 3,152,587 A | 10/1964 | Ullrich et al. | |
| 3,412,729 A | 11/1968 | Smith | |
| 4,830,014 A | 5/1989 | Goodman et al. | |
| 5,213,099 A | 5/1993 | Tripp | |
| 5,217,012 A * | 6/1993 | Young et al. ................. | 600/310 |
| 5,368,025 A | 11/1994 | Young et al. | |
| 5,413,101 A | 5/1995 | Sugiura | |
| 5,551,423 A | 9/1996 | Sugiura | |
| 5,596,986 A | 1/1997 | Goldfarb | |
| 5,611,337 A | 3/1997 | Bukta | |
| 5,673,692 A | 10/1997 | Schulze et al. | |
| 5,784,151 A | 7/1998 | Miller et al. | |
| 5,800,349 A | 9/1998 | Isaacson et al. | |
| 6,144,867 A | 11/2000 | Walker et al. | |
| 6,343,223 B1 | 1/2002 | Chin et al. | |
| 6,443,890 B1 | 9/2002 | Schulze et al. | |
| 6,454,718 B1 | 9/2002 | Clift | |
| 6,470,199 B1 | 10/2002 | Kopotic et al. | |
| 6,546,267 B1 | 4/2003 | Sugiura et al. | |
| 6,556,852 B1 | 4/2003 | Schulze et al. | |
| 6,654,622 B1 | 11/2003 | Eberhard et al. | |
| 6,694,180 B1 | 2/2004 | Boesen | |

(Continued)

FOREIGN PATENT DOCUMENTS

| | | |
|---|---|---|
| EP | 1491135 | 12/2004 |
| EP | 1830695 | 9/2007 |

(Continued)

OTHER PUBLICATIONS

U.S. Appl. No. 13/077,275, filed Mar. 31, 2011, Haisley, Charles.

(Continued)

*Primary Examiner* — Eric Winakur
*Assistant Examiner* — Marjan Fardanesh
(74) *Attorney, Agent, or Firm* — Fletcher Yoder, P.C.

(57) ABSTRACT

The present disclosure relates to sensors for use on a patient's ear. The sensors as provided may include a moldable member, such as a putty. The moldable member may be molded in place to affix the optical components of the sensor to a patient's ear tissue. For example, the moldable member may be sculpted around a curvature of a patient's earlobe. In particular embodiments, the moldable member may be activated, e.g., hardened, by exposure to particular temperatures or by exposure to light.

20 Claims, 9 Drawing Sheets

(56) References Cited

U.S. PATENT DOCUMENTS

| | | |
|---|---|---|
| 6,735,459 B2 | 5/2004 | Parker |
| 6,745,061 B1 * | 6/2004 | Hicks et al. ............... 600/344 |
| 6,760,610 B2 | 7/2004 | Tschupp et al. |
| 6,976,963 B2 | 12/2005 | Clift |
| 7,190,984 B1 | 3/2007 | DeLonzor et al. |
| 7,190,986 B1 | 3/2007 | Hannula et al. |
| 7,209,775 B2 | 4/2007 | Bae et al. |
| 7,263,396 B2 | 8/2007 | Chen et al. |
| 7,305,771 B2 | 12/2007 | Lin |
| 7,313,424 B2 * | 12/2007 | Mayevsky et al. ............ 600/310 |
| 7,341,559 B2 | 3/2008 | Schulz et al. |
| 7,356,365 B2 | 4/2008 | Schurman |
| 7,606,606 B2 | 10/2009 | Laakkonen |
| 7,658,716 B2 | 2/2010 | Banet et al. |
| 2002/0026109 A1 | 2/2002 | Diab et al. |
| 2003/0032891 A1 * | 2/2003 | Jenkins ..................... 600/546 |
| 2003/0199945 A1 | 10/2003 | Ciulla |
| 2004/0054291 A1 | 3/2004 | Schulz et al. |
| 2004/0166171 A1 | 8/2004 | McGrath et al. |
| 2005/0209516 A1 | 9/2005 | Fraden |
| 2005/0261598 A1 | 11/2005 | Banet et al. |
| 2007/0073125 A1 | 3/2007 | Hoarau et al. |
| 2007/0100218 A1 | 5/2007 | Sweitzer et al. |
| 2007/0100219 A1 | 5/2007 | Sweitzer et al. |
| 2007/0185393 A1 | 8/2007 | Zhou et al. |
| 2007/0260131 A1 | 11/2007 | Chin |
| 2008/0051670 A1 | 2/2008 | Banet et al. |
| 2008/0058614 A1 | 3/2008 | Banet et al. |
| 2010/0217103 A1 | 8/2010 | Abdul-Hafiz et al. |

FOREIGN PATENT DOCUMENTS

| | | |
|---|---|---|
| EP | 1905356 | 4/2008 |
| JP | 2003310580 A | 11/2003 |
| JP | 2004194908 A | 7/2004 |
| JP | 2006212161 A | 8/2006 |
| JP | 2003818211 B2 | 9/2006 |
| JP | 2006315467 A | 11/2006 |
| JP | 2008119288 A2 | 5/2008 |
| WO | WO 2006/064399 A1 | 6/2006 |
| WO | WO 2007013054 A1 | 2/2007 |

OTHER PUBLICATIONS

U.S. Appl. No. 13/077,299, filed Mar. 31, 2011, Haisley, Charles.

* cited by examiner

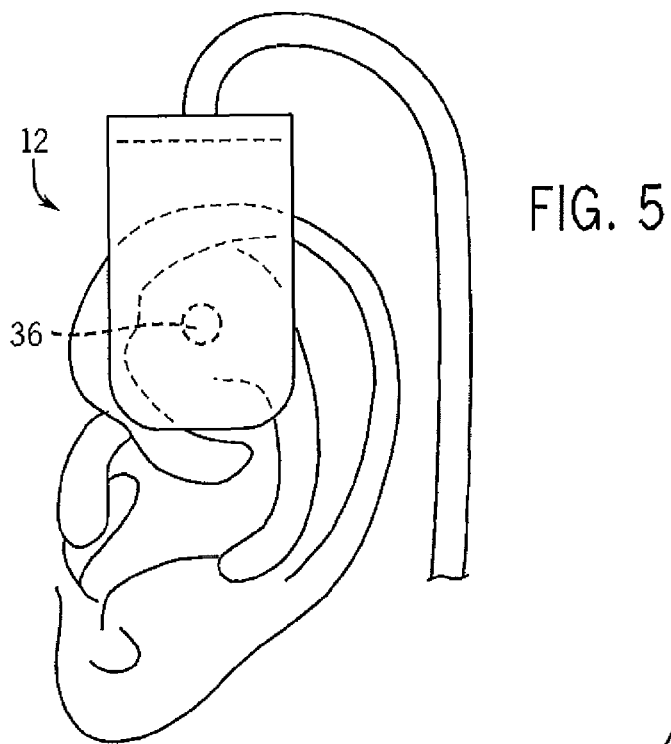
FIG. 5
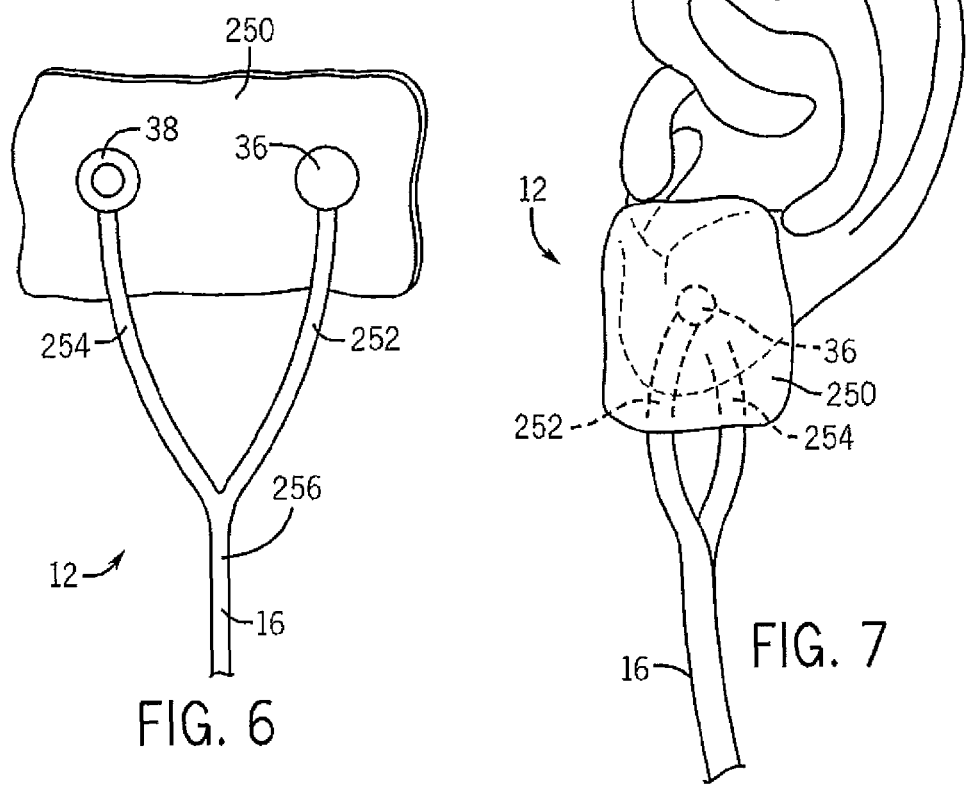
FIG. 6
FIG. 7

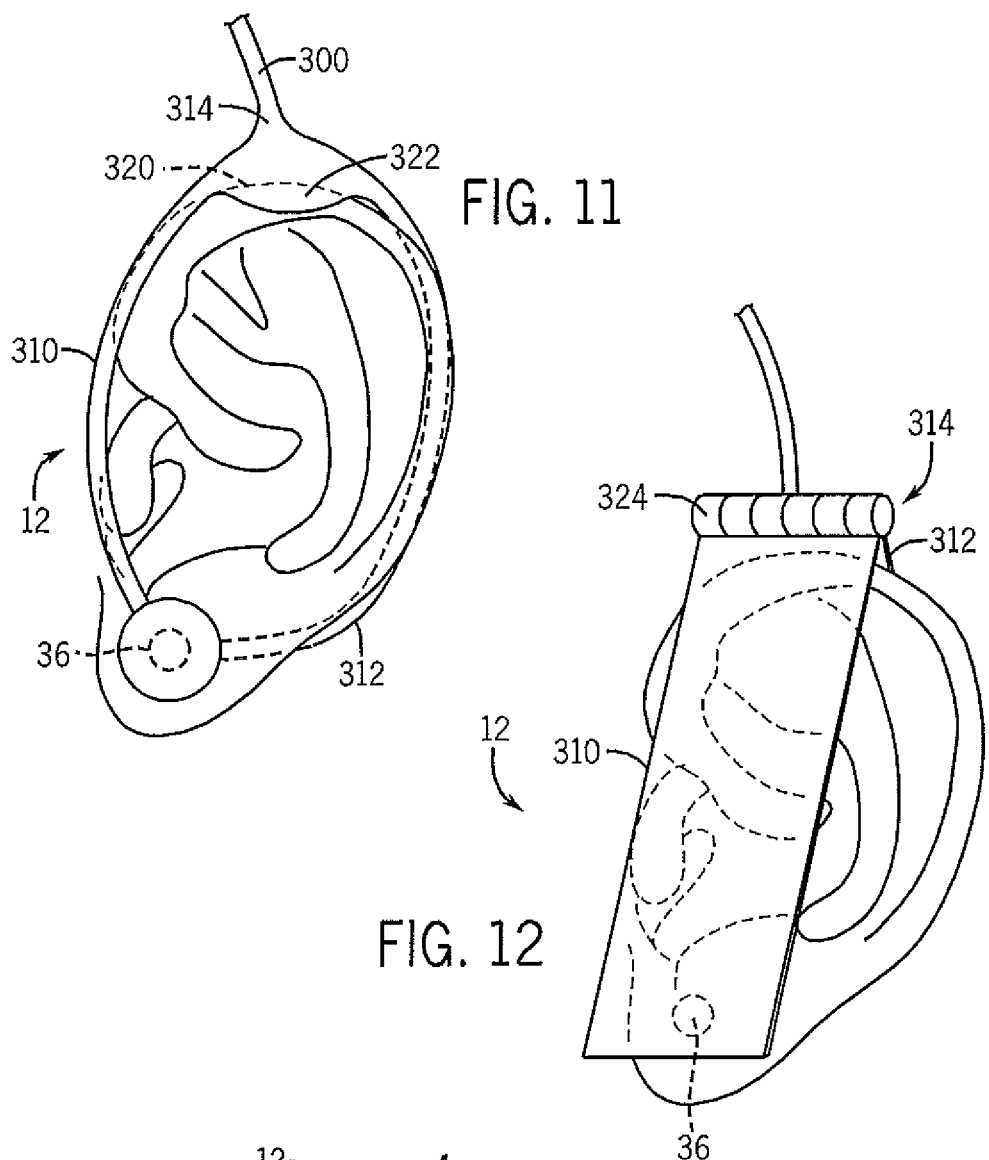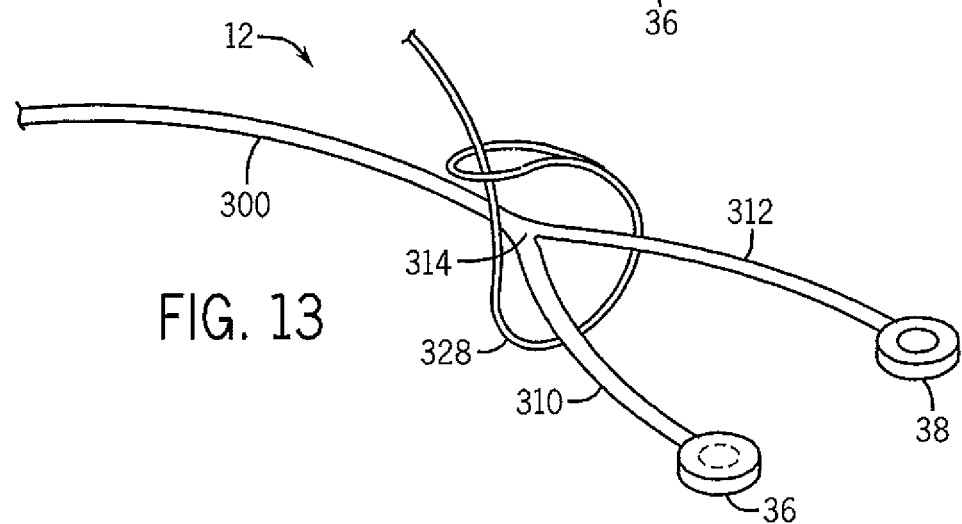

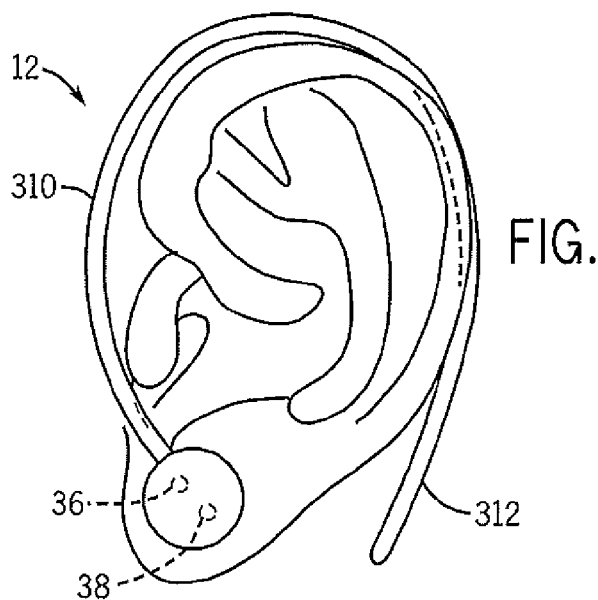
FIG. 16
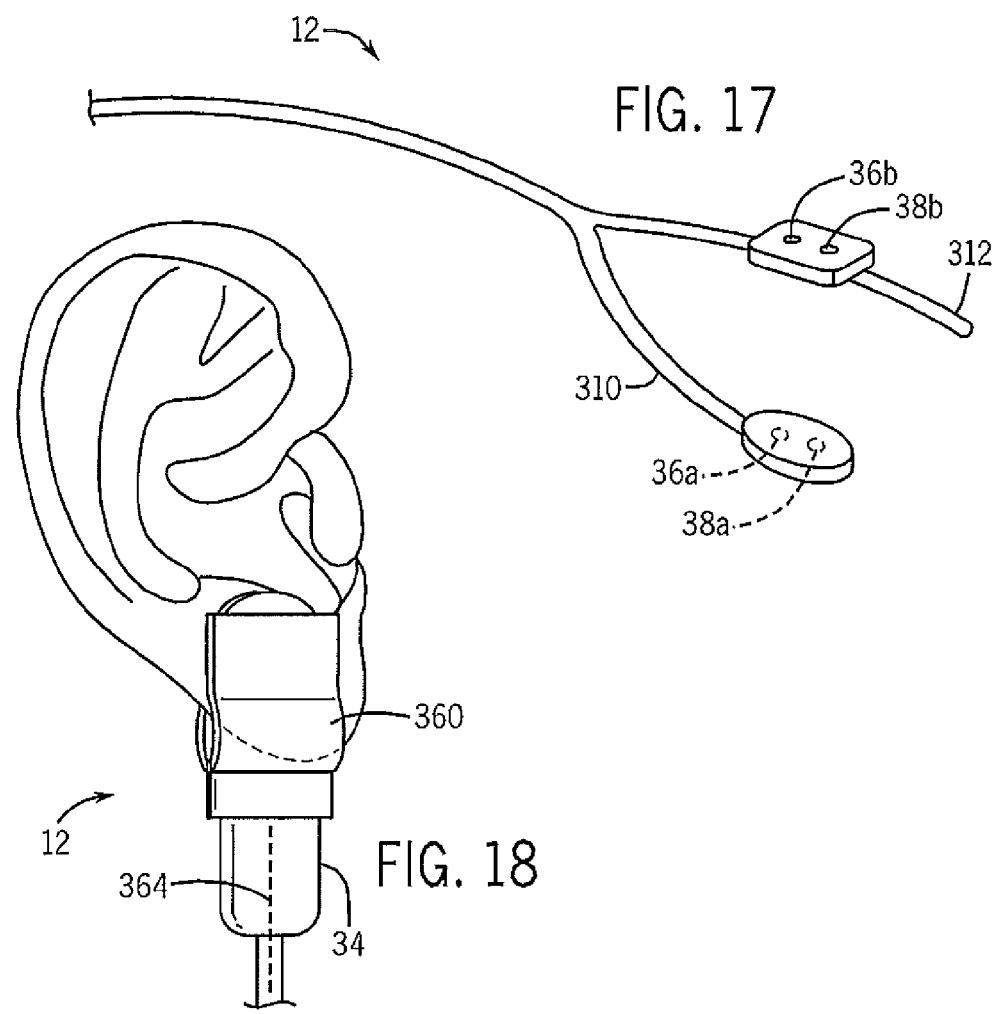
FIG. 17
FIG. 18 a
MOLDABLE EAR SENSOR

BACKGROUND

The present disclosure relates generally to medical devices and, more particularly, to medical sensors with strain relief properties that may be applied to a patient's ear for sensing physiological parameters.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximetry sensors, as well as other types of non-invasive optical sensors, transmit light through a patient's tissue and photoelectrically detect the absorption and/or scattering of the transmitted light in such tissue. One or more physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Accurate sensor measurements depend on the secure placement of the sensor on the desired measurement site on a patient. For example, a poor fit of the sensor with the tissue may allow ambient light to reach the photodetecting elements of the sensor, which may introduce error into the measurements. In addition, a poorly conforming sensor may become dislodged. To that end, sensors are manufactured with patient anatomy in mind. That is, sensors may be designed for a particular tissue placement site, e.g., a finger, and often for a particular type or size of patient, e.g., an adult. However, in critical care situations, an operator may apply a finger sensor to a patient's ear, which may result in inaccurate sensor measurements.

BRIEF DESCRIPTION OF THE DRAWINGS

Advantages of the disclosed techniques may become apparent upon reading the following detailed description and upon reference to the drawings in which:

FIG. 5 is a perspective view of the sensor of FIG. 3 applied to an upper ear region;

FIG. 6 is a perspective view of a flexible cable sensor;

FIG. 7 is a is a perspective view of the senor of FIG. 6 applied to an ear;

FIG. 11 is a is a perspective view of the sensor of FIG. 10 applied to an ear;

FIG. 12 is a perspective view of a Y-shaped clip-type sensor applied to a patient's ear;

FIG. 13 is a perspective view of a Y-shaped sensor that includes a cinching mechanism.

FIG. 16 is a perspective view of a Y-shaped reflectance-type sensor with a stabilizing branch applied to a patient's ear;

FIG. 17 is a perspective view of a Y-shaped reflectance-type sensor with a second reflectance-type sensor on an opposing branch applied to a patient's ear;

FIG. 18 is a perspective view of an ear sensor including a sliding clip applied to a patient's ear;

DETAILED DESCRIPTION OF SPECIFIC EMBODIMENTS

Figure 1:
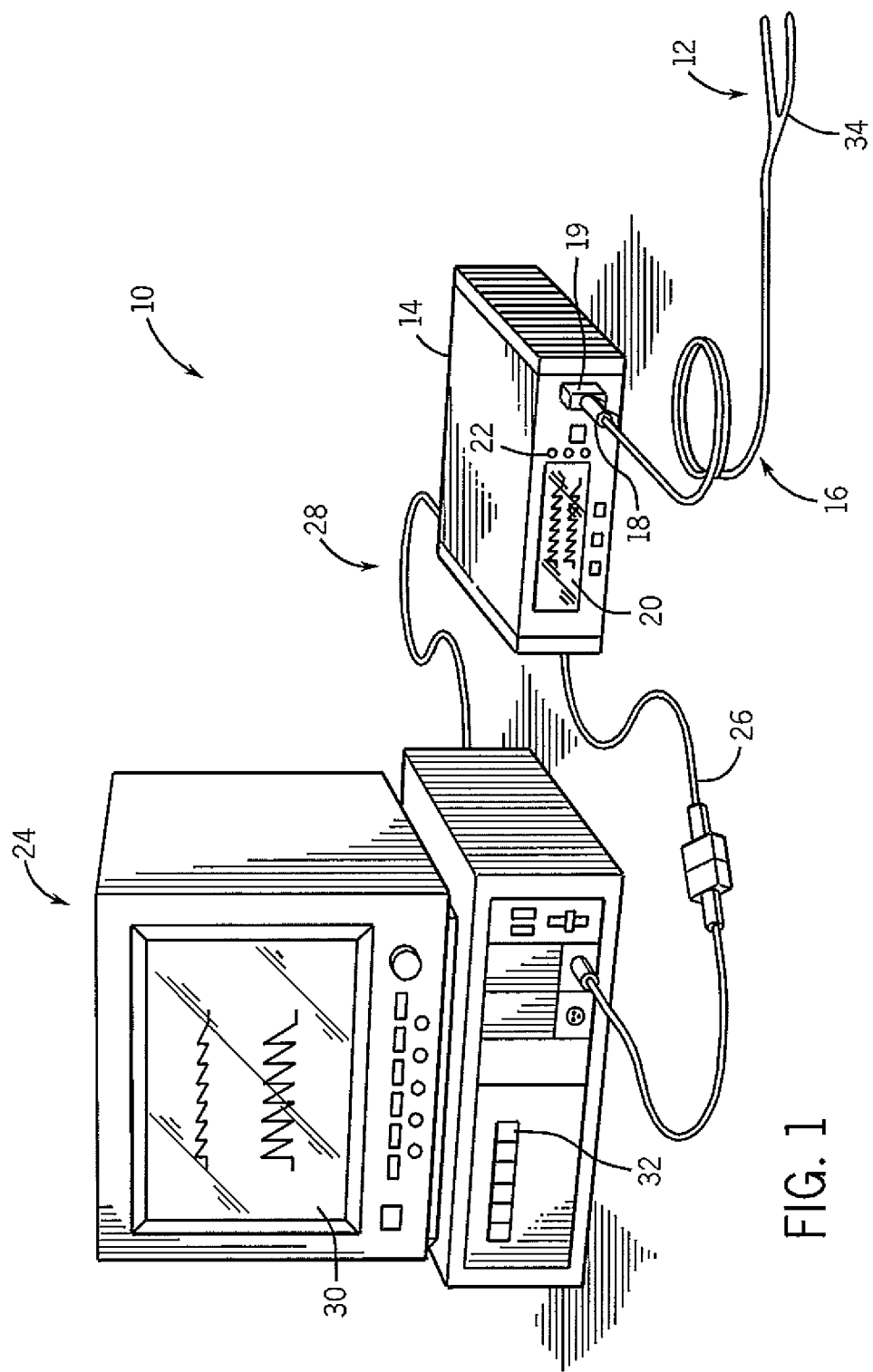
FIG. 1 illustrates a perspective view of a pulse oximetry system in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Medical sensors for sensing blood characteristics, such as arterial oxygen saturation measurement ($SpO_2$), may be placed on a patient in a location that is normally perfused with arterial blood. Common sensor placement sites include a patient's fingertips, toes, forehead, or earlobes. Often, a caregiver determines the appropriate placement of a sensor on a patient-by-patient basis. For example, a caregiver may initially apply a sensor to a patient's finger. If the sensor does not yield high quality measurements, e.g. because the patient is cold and his fingers are poorly perfused, the caregiver may then move the sensor to another tissue site, such as the ear. Rather than obtaining a new sensor for the new location, caregivers may attempt to adapt the original finger sensor for placement on the earlobe. This is particularly true for cases in which a disposable bandage-type finger sensor has been applied to the patient. While clip-type finger sensors may be too bulky to be easily placed on other tissue locations, bandage-type finger sensors are generally conformable. However, despite their conformability, bandage-type finger sensors are specifically calibrated for use on the finger. In addition, these finger sensors are too large to conform well to an earlobe and tend to peel off the earlobe under the weight of the sensor cable. Accordingly, the use of bandage-type finger sensors on the earlobe may result in measurement inaccuracies. While clip-style sensors are available that are designed to be used on a patient's ear, these sensors are reusable and are, therefore, more expensive than bandage-type sensors. In addition, clip-type sensors may be somewhat uncomfortable for a patient because of their rigidity and associated weight.

Provided herein are disposable sensors for use on a patient's ear. These sensors provide the convenience of a reusable sensor while also conforming to the ear with sufficient pressure to facilitate accurate measurements. In particular embodiments, the ear sensors include attachment features such as movable clips. In other embodiments, the sensors include features that mitigate strain introduced by a cable or electrical connector. In additional embodiments, the sensors provided herein may include deformable features that may be specifically molded to the patient anatomy. For example, the sensors may include moldable putty that may be molded around the ear to affix the sensor to the patient.

With this in mind, FIG. 1 depicts an embodiment of a patient monitoring system 10 that may be used in conjunction with a medical sensor 12. Although the depicted embodiments relate to sensors for use on a patient's ear, it should be understood that, in certain embodiments, the strain relief features and/or attachment features of the sensor 12 as provided herein may be incorporated into sensors for use on other tissue locations, such as the finger, the toes, the heel, the forehead, or any other appropriate measurement site. In addition, although the embodiment of the patient monitoring system 10 illustrated in FIG. 1 relates to photoplethysmography or pulse oximetry, the system 10 may be configured to obtain a variety of medical measurements with a suitable medical sensor. For example, the system 10 may, additionally or alternatively, be configured to determine patient temperature, transvascular fluid exchange volumes, tissue hydration, blood flow, cardiovascular effort, glucose levels, level of consciousness, total hematocrit, hydration, electrocardiography, electroencephalograpy, or any other suitable physiological parameter. As noted, the system 10 includes the sensor 12 that is communicatively coupled to a patient monitor 14 via a cable 16 through a plug 18 coupled to a sensor port 19. Additionally, the monitor 14 includes a monitor display 20 configured to display information regarding the physiological parameters, information about the system, and/or alarm indications. The monitor 14 may include various input components 22, such as knobs, switches, keys and keypads, buttons, etc., to provide for operation and configuration of the monitor. The monitor 14 also includes a processor that may be used to execute code such as code for implementing the techniques discussed herein.

The monitor 14 may be any suitable monitor, such as a pulse oximetry monitor available from Nellcor Puritan Bennett LLC. Furthermore, to upgrade conventional operation provided by the monitor 14 to provide additional functions, the monitor 14 may be coupled to a multi-parameter patient monitor 24 via a cable 26 connected to a sensor input port or via a cable 28 connected to a digital communication port. In addition to the monitor 14, or alternatively, the multi-parameter patient monitor 24 may be configured to calculate physiological parameters and to provide a central display 30 for the visualization of information from the monitor 14 and from other medical monitoring devices or systems. The multi-parameter monitor 24 includes a processor that may be configured to execute code. The multi-parameter monitor 24 may also include various input components 32, such as knobs, switches, keys and keypads, buttons, etc., to provide for operation and configuration of the a multi-parameter monitor 24. In addition, the monitor 14 and/or the multi-parameter monitor 24 may be connected to a network to enable the sharing of information with servers or other workstations.

The sensor 12 may be any sensor suitable for detection of any physiological parameter. The sensor 12 may include optical components (e.g., one or more emitters and detectors), acoustic transducers or microphones, electrodes for measuring electrical activity or potentials (such as for electrocardiography), pressure sensors, motion sensors, temperature sensors, etc. In one embodiment, the sensor 12 may be configured for photo-electric detection of blood and tissue constituents. For example, the sensor 12 may be a pulse oximetry sensor, such as those available from Nellcor Puritan Bennett LLC. As shown in FIG. 1, the sensor 12 may be a bandage-type sensor having a generally flexible sensor body to enable conformable application of the sensor to a sensor site on a patient. However, in particular embodiments, certain aspects of the present disclosure may be used in conjunction with relatively rigid clip-type sensors. For example, clip-type sensors may benefit from the inclusion of moldable components that may prevent ambient light from reaching the optical components of the sensor 12.

In one embodiment, the sensor 12 may include a sensor body 34 housing the optical components (e.g., an emitter for emitting light at certain wavelengths into a tissue of a patient and a detector for detecting the light after it is reflected and/or absorbed by the blood and/or tissue of the patient) of the sensor. In certain embodiments, the sensor 12 may be a wireless sensor 12. Accordingly, the wireless sensor 12 may establish a wireless communication with the patient monitor 14 and/or the multi-parameter patient monitor 24 using any suitable wireless standard. By way of example, the wireless module may be capable of communicating using one or more of the ZigBee standard, WirelessHART standard, Bluetooth standard, IEEE 802.11x standards, or MiWi standard. In embodiments in which the sensor 12 is configured for wireless communication, the strain relief features of the cable 16 may be housed in the sensor body 34.

Figure 2:
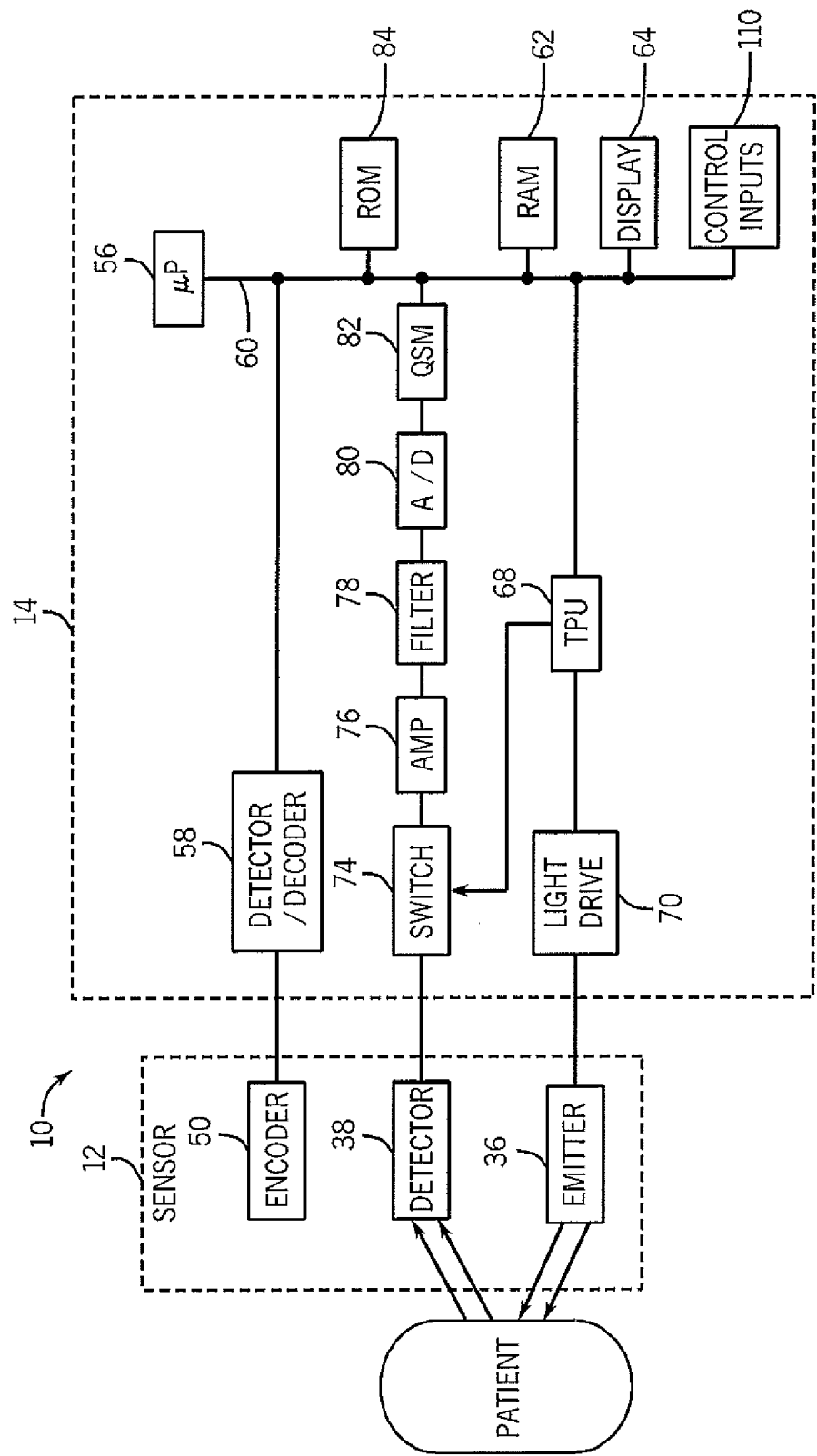
FIG. 2 is a block diagram of the pulse oximetry system of FIG. 1.

Turning to FIG. 2, a simplified block diagram of the medical system 10 is illustrated in accordance with an embodiment. The sensor 12 may include optical components such as an emitter 36 and a detector 38. In addition, the sensor 12 may include an encoder 50. The emitter 36 and the detector 38 may be arranged in a reflectance or transmission-type configuration with respect to one another. It should be noted that the emitter 36 may be capable of emitting at least two wavelengths of light, e.g., red and infrared am light, into the tissue of a patient, where the red wavelength may be between about 600 nanometers (nm) and about 700 nm, and the IR wavelength may be between about 800 nm and about 1000 nm. The emitter 36 may include a single emitting device, for example, with two light emitting diodes (LEDs) or the emitter 36 may include a plurality of emitting devices with, for example, multiple LED's at various locations. In some embodiments, the LEDs of the emitter 36 may emit three or more different wavelengths of light. Such wavelengths may include a red wavelength of between approximately 620-700 nm (e.g., 660 nm), a far red wavelength of between approximately 690-770 nm (e.g., 730 nm), and an infrared wavelength of between approximately 860-940 nm (e.g., 900 nm). Other wavelengths may include, for example, wavelengths of between approximately 500-600 nm and/or 1000-1100 nm. Regardless of the number of emitting devices, light from the emitter 36 may be used to measure, for example, oxygen saturation, water fractions, hematocrit, or other physiologic parameters of the patient. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In one embodiment, the detector 38 may be an array of detector elements capable of detecting light at various intensities and wavelengths. In one embodiment, light enters the detector 38 after passing through the tissue of the patient or being reflected by elements in the patent's tissue. The intensity of the received light may be directly related to the absorbance and/or reflectance of light in the tissue of the patient. That is, when more light is absorbed by the tissue, less light is available to be received by the detector 38. After converting the received light to an electrical signal, the detector 38 may send the signal to the monitor 14, where physiological characteristics may be calculated based at least in part on the absorption and/or reflection of light by the tissue of the patient.

In certain embodiments, the medical sensor 12 may also include an encoder 50 that may provide signals indicative of the wavelength of one or more light sources of the emitter 36, which may allow for selection of appropriate calibration coefficients for calculating a physical parameter such as blood oxygen saturation. The encoder 50 may, for instance, be a coded resistor, EEPROM or other coding devices (such as a capacitor, inductor, PROM, RFID, parallel resident currents, or a colorimetric indicator) that may provide a signal to a microprocessor 56 related to the characteristics of the medical sensor 12 to enable the microprocessor 56 to determine the appropriate calibration characteristics of the medical sensor 12. Further, the encoder 50 may include encryption coding that prevents a disposable part of the medical sensor 12 from being recognized by a microprocessor 56 unable to decode the encryption. For example, a detector/decoder 58 may translate information from the encoder 50 before it can be properly handled by the processor 56. In some embodiments, the encoder 50 and/or the detector/decoder 58 may not be present.

Signals from the detector 38 and/or the encoder 50 may be transmitted to the monitor 14. The monitor 14 may include one or more processors 56 coupled to an internal bus 60. Also connected to the bus may be a RAM memory 62 and a display 64. A time processing unit (TPU) 68 may provide timing control signals to light drive circuitry 70, which controls when the emitter 36 is activated, and if multiple light sources are used, the multiplexed timing for the different light sources. TPU 68 may also control the gating-in of signals from detector 38 through a switching circuit 74. These signals are sampled at the proper time, depending at least in part upon which of multiple light sources is activated, if multiple light sources are used. The received signal from the detector 38 may be passed through an amplifier 76, a low pass filter 78, and an analog-to-digital converter 80 for amplifying, filtering, and digitizing the electrical signals the from the ear sensor 12. The digital data may then be stored in a queued serial module (QSM) 82, for later downloading to RAM 62 as QSM 82 fills up. In an embodiment, there may be multiple parallel paths for separate amplifiers, filters, and A/D converters for multiple light wavelengths or spectra received.

In an embodiment, based at least in part upon the received signals corresponding to the light received by detector 38, processor 56 may calculate the oxygen saturation using various algorithms. These algorithms may use coefficients, which may be empirically determined. For example, algorithms relating to the distance between an emitter 36 and various detector elements in a detector 38 may be stored in a ROM 84 and accessed and operated according to processor 56 instructions.

Furthermore, one or more functions of the monitor 14 may also be implemented directly in the sensor 12. For example, in some embodiments, the sensor 12 may include one or more processing components capable of calculating the physiological characteristics from the signals obtained from the patient. In accordance with the present techniques, the sensor 12 may be configured to provide optimal contact between a patient, the detector 38, and/or the emitter 36, may have varying levels of processing power, and may output data in various stages to the monitor 14, either wirelessly or via the cable 16. For example, in some embodiments, the data output to the monitor 14 may be analog signals, such as detected light signals (e.g., pulse oximetry signals), or processed data.

Sensors 12 as provided herein may be applied to a patient's ear to generate a signal related to a physiological parameter. In particular, the disclosed sensors 12 may be securely and comfortably attached to the ear with reduced strain on the electrical components. For example, for relatively rigid clip-type sensors, the weight of the sensor housing components may introduce strain on the cable, which in turn may result in movement of the sensor relative to the tissue and inaccuracies in the measured signal. In addition, ear sensors are typically positioned with the cable hanging down from the sensor, and gravity may exacerbate the effects of such strain. Even for patients in a supine position, the cable tends to hang down from the ear, which puts pressure on both the sensor and the tissue itself. The disclosed sensors 12 provide flexibility in the positioning and attachment of the sensing components to the ear, which may result in decreased strain on the sensor 12.

In particular embodiments, the sensors 12 may include moldable members that may be shaped and molded around the irregular profile of the ear. Such sensors 12 may be shaped around the tissue at the time of application to the patient, which facilitates a secure and conforming fit for a patient regardless of individual anatomy. In addition, the moldable members may seal any light paths from outside of the sensor and may provide flexible and custom-fitted shunt barriers to prevent shunting of light from the emitter 36 to the detector 38. While bandage-type sensors are generally conformable, such sensors still retain enough rigidity that ambient light may leak into the sensor. Sensors with moldable members may create a tissue-contact surface that bends around the tissue to protect the detector from any undesired light.

Moldable members as provided may include putties, clays, polymers, or waxes that are deformable by an operator (e.g., easily deformed by hand). For example, the moldable members may include impression wax or wax compositions, hydrocolloidal impression masses and rubber impression masses. The molding material may further be a gelatin or agar having a calcium sulfate reactor. In one embodiment, the moldable material may be a dental impression material or gum-type composition. In other embodiments, the moldable member may be a medical paste, such as Moldable Strip Paste, (Coloplast, Minn.). The moldable material may also be characterized by its hardness on the Shore OO scale. For example, in one embodiment, the moldable member may have a hardness of less than 40 Shore OO or less than 20 Shore OO. In certain embodiments, the moldable member may be configured to harden or cure upon exposure a specific wavelength of light, heat, or a chemical catalyst for hardening. Examples of suitable material include Triad® light-curing materials (DENTSPLY, Pa.). In particular embodiments, room temperature vulcanizing silicones may be used to form the moldable member. In such embodiments, the moldable member may not only provide a conforming fit, but may also contribute to the overall rigidity of the sensor 12 and may provide a fixed optical distance between the emitter 36 and the detector 38. In this manner, a sensor 12 may combine the tissue-conforming advantages of bandage-type sensors with the stability and motion-resistance of more rigid sensors. In another embodiment, to facilitate the appropriate interaction with undesired light, the moldable member may be opaque and/or dark in color.

Figure 3:
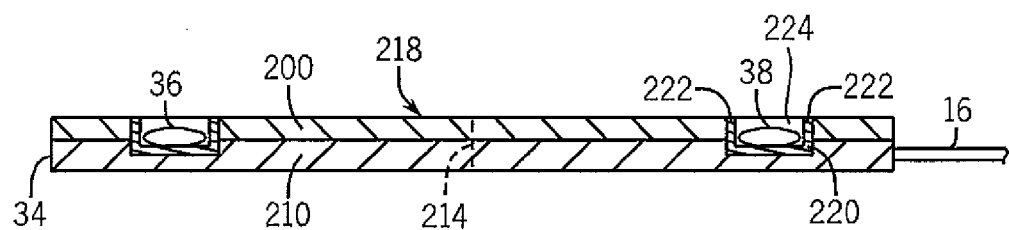
FIG. 3 is a section view of an ear sensor including a moldable layer.

FIG. 3 is a section view of a transmission-type sensor 12 including a moldable layer 200. As depicted, the sensor body 34 may also include a backing layer 210 that is generally conformable. For example, the backing layer 210 may be one or more cloth or bandage layers. Alternatively, the backing layer 210 may be relatively resilient and may be scored or hinged at a fold point 214 to facilitate bending or folding of the sensor body 34 around the tissue. For example, a relatively rigid clip-type sensor may benefit from an interior moldable layer 200, which may prevent light leakage onto the detector 38 by filling in any gaps between the sensor 12 and the tissue. The cable 16, or other suitable electrical connector, may be embedded in or otherwise coupled to the backing layer 210. The backing layer 210 may also include suitable coatings or shielding layers for preventing cross-talk between the electrical couplings of the emitter 36 and the detector 38.

The moldable layer 200 is disposed on a tissue-contacting surface 218 of the sensor body 34 such that the moldable layer 34 is in direct contact with the tissue when the sensor 12 is applied to the patient. When the sensor is applied, an operator may squeeze or press the sensor 12 to fit the sensor around the tissue. To prevent the moldable material from migrating over the optical components, the emitter 36 and the detector 38 may be disposed within housing members 220 that include ends 222 that serve as a barrier to lateral movement of the moldable layer 200 over the optical components. The emitter 36 and detector 38 may be covered by optically transparent windows 224 that are positioned within the housing members 220. In certain embodiments, the ends 222 may be slightly raised relative to the moldable layer 200, which may facilitate shaping of the moldable layer 200 around each optical component. That is, when the sensor 12 is squeezed around the ear, the moldable layer 200 may accumulate around ends 222. In addition, the sensor body 34 may include a raised lip around all or part of the outside edge to prevent migration of the moldable layer 200 outside the sensor. In other embodiments, such migration outside the sensor may serve as a barrier to infiltration of ambient light.

The moldable layer 200 may be covered by a release layer, which may be removed, e.g., peeled off, prior to application of the sensor 12. The release layer may protect the moldable layer 200 from exposure to air, which may prematurely harden the sensor 12. The release layer may be disposed on the tissue-contacting surface 218 of the sensor 12 such that the moldable layer 200 is between the release layer and the backing layer 210. For example, the release layer and the backing layer 210 may form a substantially air-tight seal around the moldable layer 200. In addition, in embodiments in which the moldable layer 200 is tacky, adhesive, or coated in an adhesive layer, the release layer may prevent self-adhesion of the sensor 12 prior to application.

Figure 4:
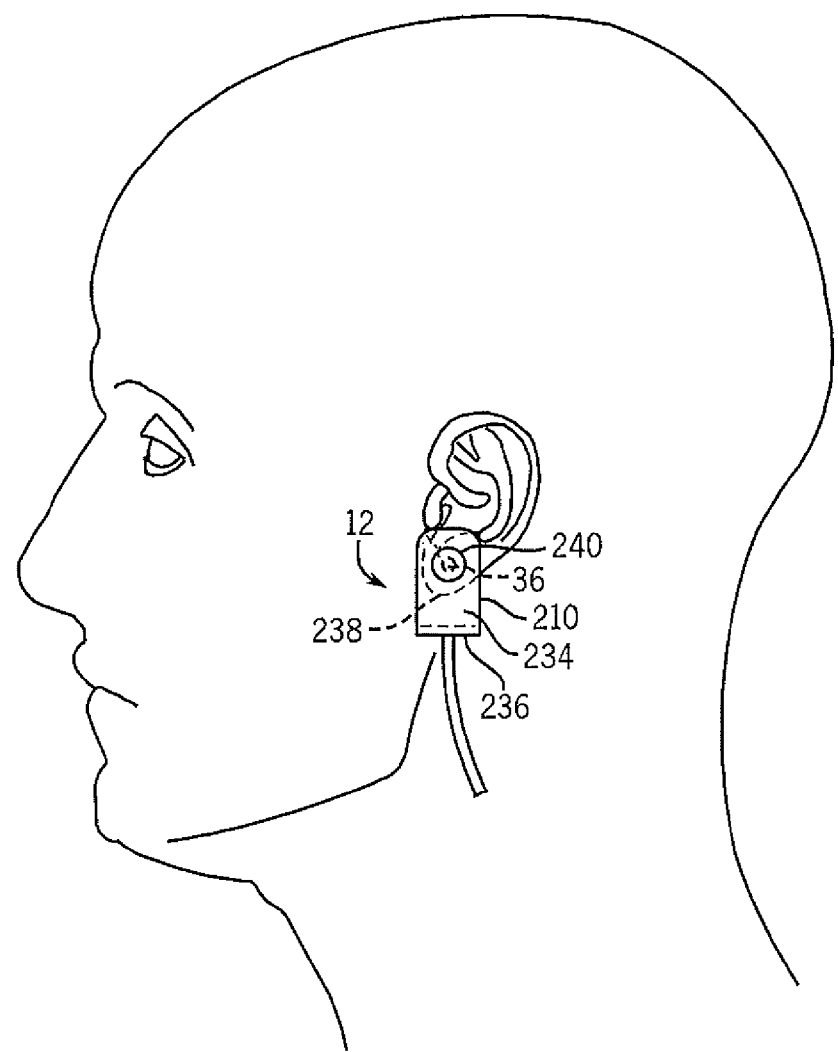
FIG. 4 is a perspective view of the sensor of FIG. 3 applied to an earlobe.

FIG. 4 is a perspective view of the sensor 12 of FIG. 3 applied to a patient's ear. The sensor 12 is bent around the earlobe such the emitter 36 and the detector 38 are aligned on opposing sides of the earlobe. The moldable layer 200 is on the interior of the sensor in contact with the tissue. To facilitate the positioning of the sensor, the exterior, i.e., visible to an observer when the sensor 12 is applied, the exterior surface 234 of the sensor 12 may include one or more alignment indicators. For example, a folding indicator 236 on the fold point 214 may indicate the location of the sensor body that is configured to be positioned on an underside 238 of the earlobe. In addition, optical component indicators 240 may be positioned at locations on the exterior surface 234 that correspond to the emitter 36 and the detector 38. In a particular embodiment, the sensor 12 may include magnetic components that are configured to align the emitter 36 and detector 38. For example, the optical housing members 220 (see FIG. 3) may include magnetic features. When the optical housing members 220 are positioned correctly on opposing sides of the earlobe, the housing members 220 experience a maximum of magnetic force and are more difficult to pull apart, indicating proper alignment to an operator. In addition, the sensor 12 may be cured or hardened in place on the patient, for example by exposing the sensor 12 to a harmless wavelength of light.

While the sensor 12 may be applied to an earlobe, depending on the configuration of the sensor body, the sensor 12 may be bent around other parts of the ear, such as an upper curve, i.e., a helix, as shown in FIG. 5, or the tragus. In addition, the disclosed features may also be incorporated into reflectance-type sensors. For example, a reflectance-type sensor may include a sensor body 34 that is configured to be wrapped around an earlobe. In such an embodiment, the emitter 36/detector 38 pair are positioned on the same side of the ear. In a particular embodiment, the sensor body 34 may include magnetic components configured to mate across the tissue. In such an embodiment, one magnetic component on one side of the earlobe may be positioned proximate to the emitter 36/detector 38 pair.

In addition to embodiments in which a moldable member may form a layer on a sensor body, in particular embodiments, the moldable member may be used instead of a sensor body or may be used to affix electrical connectors to the tissue. FIG. 6 is a perspective view an embodiment in which a moldable member 250 is used in conjunction with a Y-shaped sensor 12 formed from an electrical connector (e.g. cable 16). The emitter 36 and the detector 38 are disposed at the ends of the branches 252 and 254 of the Y-shaped member while the main body 256 extends towards the monitor. The moldable member 250 may be molded around the branches 252 and 254 to affix the sensor 12 to the patient, as shown in FIG. 7.

Figure 8:
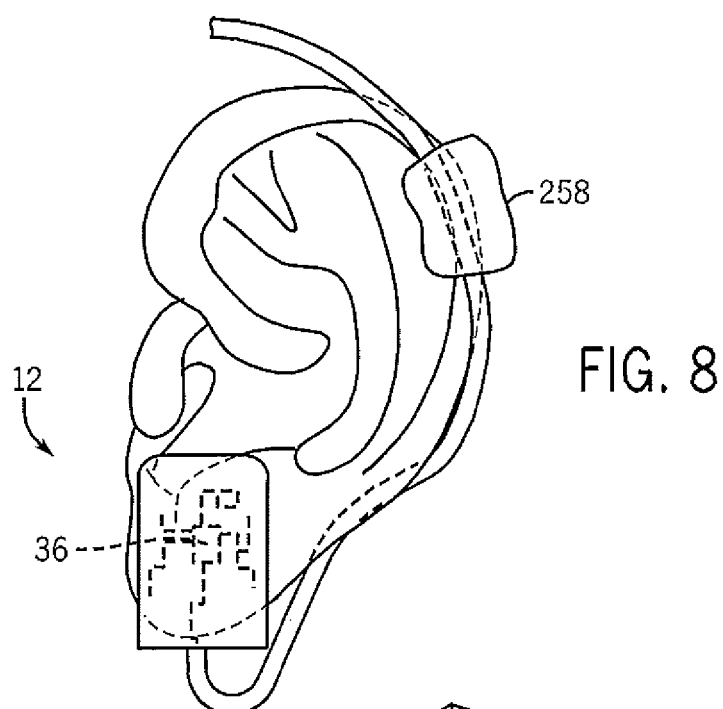
FIG. 8 is a is a perspective view of a flex circuit sensor with a moldable member applied to an ear.

In an alternative embodiment in which a sensor body 34 is formed from a flexible circuit, as shown in FIG. 8, the sensor body 34 may be affixed to the tissue with the moldable member 250. For example, the sensor body 34 may be scored at the fold line to facilitate the proper placement and alignment of the emitter 36 and detector 38. In addition, the moldable member 250 may be used to affix the cable 16 to the tissue as well to promote strain relief. As depicted, the cable 16 is affixed to the upper ear with an additional moldable member 258.

Figure 9:
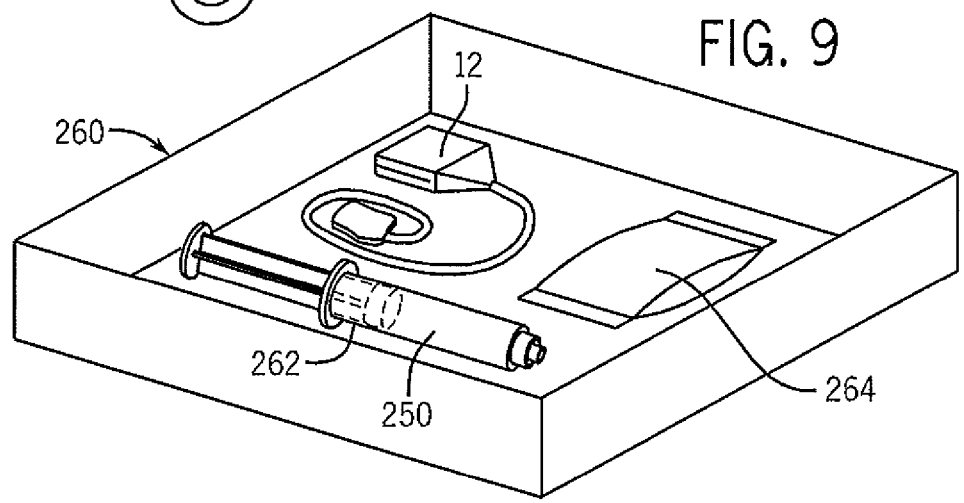
FIG. 9 is a perspective view of a moldable sensor kit.

Regardless of whether the moldable member forms a tissue-contacting layer on a sensor body 34 or a removable affixing member for the sensor 12, in certain embodiments, the sensor 12 may be provided as a kit 260 with the moldable member 250 provided as a separate component, as shown in FIG. 9. The kit may also include an appropriate applicator 262, such as a syringe, tube, or knife. In addition, where appropriate, the kit may include a curing agent 264 that may be mixed with the moldable member 250 to promote its hardening. In such embodiments, the moldable member 250 may only be deformable for a set period of time after exposure to the curing agent. The kit may also include instructions for applying the curing agent 264 and/or applying the moldable member 250 to the sensor 12.

Figure 10:
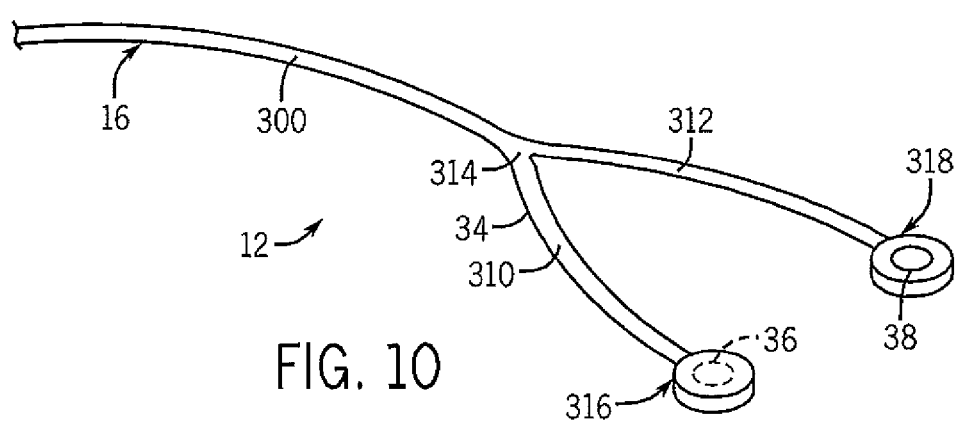
FIG. 10 is a view of a Y-shaped transmission-type sensor.

In addition to sensors that include moldable components, the sensors 12 as provided herein may include generally conformable or shapeable components to relieve strain on the sensor. FIG. 10 depicts a generally Y-shaped sensor 12 that is configured to be placed upside down on the ear, as shown in FIG. 11. As provided the sensor 12 may include a sensor body 34 that generally refers to the portion of the sensor 12 that is applied to the patient, e.g., affixed to and/or wrapped around the ear, to facilitate patient monitoring. The sensor body 34 may house the electrical connections from the emitter 36 and the detector 38. In certain embodiments, the housing or body of the cable 16 may form all or part of the sensor body 34. In one embodiment, the cable 16 may be a 2-wire cable that takes a single wire branched form in the portion that wraps around the ear. The sensor body 34 may include the branched portion and, in particular embodiments, a section of the cable 16 immediately adjacent to the branch point to form a generally Y-shaped sensor body 34. In such an embodiment, the outer plastic shield or other covering of the cable 16 may form the sensor body 34. In other embodiments, the sensor body portion of the cable 16 may be formed or shaped (e.g. flattened) to achieve a particular arrangement of the sensor body 34. In other embodiments, the sensor body may include bandage layers, surfaces for attachment to the patient, rigid outer shells, or different types of shields or housing for electrical wires or connectors.

In one embodiment, the Y-shape may include a main branch 300, a first fork 310, and a second fork 312. The main branch 300 may extend away from the ear and form the cable 16. A junction 314 of the main branch 300 with the forks 310 and 312 is positioned above the ear, and the first fork 310 and the second fork 312 run down opposite sides of the ear. The emitter 36 is positioned at an end 316 of the first fork and the detector 38 is positioned at an end 318 of the second fork 312. The electrical connectors for the emitter 36 and the detector 38 may be contained within the first fork 310 and the second fork 312 and may run along the main branch 300 into cable 16. It should also be understood that the positions of the emitter 36 and the detector 38 may be reversed. In the depicted configuration, the weight of the sensor hangs down from above the ear rather than hanging below the ear from the earlobe. This may reduce the tendency of the sensor 12 to be pulled off the ear. That is, a traditional clip-type sensor may be pulled off by a downward tug on the cable. However, an upside-down Y-shape is less vulnerable to being pulled off because the cable 16 does not hang down from the ear. In addition, the attachment points of the sensor 12 may be positioned on the head or neck and not the ear. This reduces the effects of motion on the sensor because tugs on the cable 16 pull at the attachment points, and not on the emitter 36 and the detector 38.

As shown in FIG. 11, the junction 314 may rest on a top 320 of the ear. The sensor 12 may form a curve 322 that is shaped to conform to the top 320 of the ear, e.g., the curve 322 may conform to the thickness and curvature of the tissue at the top of the ear. Accordingly, the top 320 of the ear may hold some of the weight of the sensor. The sensor may also be adhered to the tissue along the main branch 300 or the first fork 310 and the second fork 312. In addition, the emitter 36 and the detector 38 may be coated with an adhesive to facilitate attachment to the tissue. Magnetic components or moldable components may be employed to facilitate attachment of the sensor 12. In the embodiment shown in FIG. 12, the junction 314 may form a hinge 324 (e.g., a spring clip or a spring-loaded hinge) such that first fork 310 and the second form 312 may be biased towards one another. In such an embodiment, the first fork 310 and the second fork 312 may be formed from relatively rigid materials.

The first fork 310 and the second fork 312 may be substantially equal in length. In another embodiment, the second fork 312 may be a different length than the first fork 310. For example, depending on the path of the second fork 312 along the back of the ear, the second fork 312 may be longer than the first fork 310. The first fork 310 and the second fork may be about a length of an average ear, from the earlobe 330 to the top 320 of the ear. In a particular embodiment, the first fork 310 and the second fork 312 may be at least about 1 inch in length, or may be between 1 inch and 4 inches in length.

The Y-shaped sensor 12 may be formed all or in part from conformable or shapeable materials. It particular embodiments, the materials may include traditional medical sensor materials and shielded cable or wire materials that may be placed directly against a patient's skin. For example, in one embodiment, the main branch 300, the first fork 310, and the second fork 312 are all formed from a flexible cable. In other embodiments, the Y-shaped sensor 12 may include a flexible circuit. In another embodiment, first fork 310 and the second fork 312 form a sensor body 34 and are a different material than the main branch 300. In such an embodiment, the curve 322 may be relatively rigid while the rest of the sensor body 34 is flexible, or the entire sensor body 34 may be relatively rigid while the main branch 300 is conformable. In yet another embodiment, the main branch 300 is relatively rigid at least for a portion of its length adjacent to the junction 314. In another specific embodiment, the first fork 310 and/or the second fork 312 are formed from shapeable wires. That is, the first fork 310 and/or the second fork 312 may be bent around the ear, but the wires, one bent, tend to hold their position. In this manner, the sensor 12 may be formed to the shape of a particular patient's ear.

FIG. 13 illustrates an embodiment in which the sensor 12 includes a cinching mechanism 328 that may pull the first fork 310 and the second fork 312 taut against the ear. The cinching mechanism may be a loop that slides down over the junction 314 and is capable of being tightened to hold the first fork 310 and the second fork 312 at a desired position. In such an embodiment, the first fork 310 and the second fork 312 may be relatively conformable. The cinching mechanism 328 may be a knotted loop that becomes tighter as it slides further down the main branch 300. In other embodiments, the cinching mechanism may have teeth or other adjustment features to fix its diameter around the first fork 310 and the second fork 312, similar to a zip tie.

Figure 14:
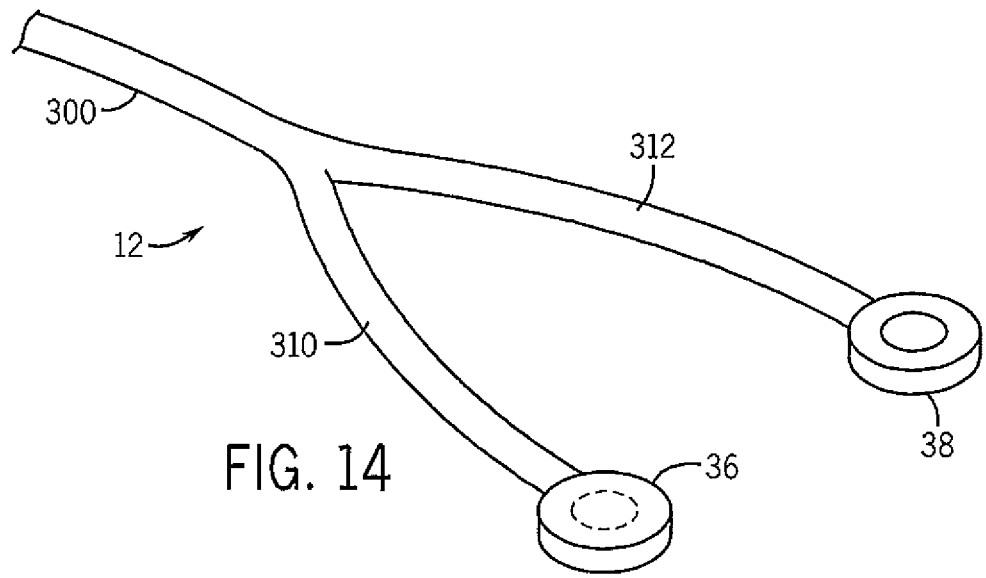
FIG. 14 is a perspective view of a Y-shaped sensor with flat cables.
Figure 15:
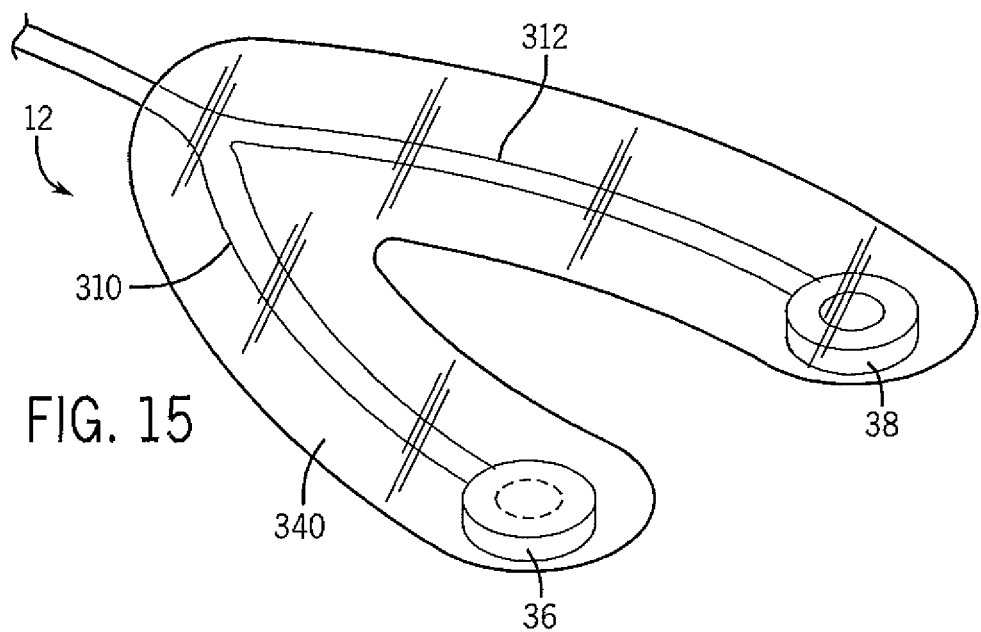
FIG. 15 is a perspective view of a Y-shaped reflectance-type sensor including an adhesive layer.

A Y-shaped sensor as provided may have a relatively low profile to provide a more comfortable fit for the patient. In certain embodiments, all or part of the sensor 12 is formed from substantially flat cables. FIG. 14 is a perspective view of a Y-shaped sensor 12 with flat portions along the main branch 300, the first fork 310, and the second fork 312. Flat cables may conform to the tissue better than rounded structures. In addition, a relatively flat surface may provide increased surface area for an adhesive. Alternatively, the sensor 12 may include an adhesive layer 340, as shown in FIG. 15, that extends away from the sensor 12 to provide more surface area for adhesion. In particular, the adhesive layer 340 may be highly flexible to facilitate a conforming fit. In addition, the adhesive layer 340 may be transparent so that an operator may easily view the sensor 12 during application.

A Y-shaped sensor 12 may also be implemented in a reflectance-type configuration. For example, rather than an opposing emitter 36 and detector 38, an emitter 36/detector 38 pair may be positioned on a single fork. The opposing fork may be used to stabilize the attachment of the sensor 12. FIG. 16 is a perspective view of a Y-shaped reflectance-type sensor with a stabilizing branch applied to a patient's ear. As shown, the emitter 36 and the detector 38 are disposed on the first fork 310, which runs along the front of the ear. The second fork 312 runs behind the ear and is affixed to the neck. The second fork 312 stabilizes the sensor 12 and may be formed from more rigid materials relative to the first fork 310. In other embodiments, the second fork 312 may include a magnetic component configured to align across the tissue of the ear with a magnetic component on the first fork 310.

FIG. 17 is a perspective view of a Y-shaped reflectance-type sensor 12 with a plurality of optical components. In the depicted configuration, the first fork 310 includes a first emitter 36a and first detector 38a and the second fork 312 includes a second emitter 36b and a second detector 38b. The emitter/detector pairs may be offset from one another along the ear so that they may operate simultaneously without interfering with one another. Alternatively, the timing of the emitter/detector pairs may be controlled via the monitor 14 so that they are configured to emit and detect light at different times. In other implementations, the sensor 12 may include a transmission-type sensing arrangement as well as a reflectance-type sensing arrangement or two transmission-type arrangements. Further, the first emitter 36a and first detector 38a and the second emitter 36b and a second detector 38b may both be configured to sense the same physiological parameter. That is, the depicted configuration may allow measurement of oxygen saturation at two different sites on the ear. The monitor 14 may arbitrate the signals to determine which measurement site has the highest quality measurements. In other embodiments, the emitter/detector pairs may be configured to sense different physiological parameters. For example, the first emitter 36a and first detector 38a may be configured for pulse oximetry while the second emitter 36b and a second detector 38b may be configured for determining a tissue water fraction.

Sensors 12 with improved strain relief properties may also include sensor configurations with a traditional clip-type arrangement in which the sensor cable 16 hangs down from the earlobe. As noted, this configuration may introduce strain from the weight of the electrical connectors as well as the weight of the sensor housing. In certain embodiments, the pull of the sensor 12 may be mitigated by reducing the weight of the sensor components and the attachment mechanism. Provided herein are sensors 12 that combine conformable bandage-type sensor bodies 34 with lightweight rigid clips. FIG. 18 is a perspective view of an ear sensor 12 with a sliding clip 360 applied to a patient's ear. It is envisioned that the depicted sensor 12 is disposable. In the depicted embodiment, the sensor body 34 is formed from flexible bandage-type materials. The sensor cable 16 runs along an axis 364 of the sensor body 34 and extends away from the sensor 12.

Figure 19:
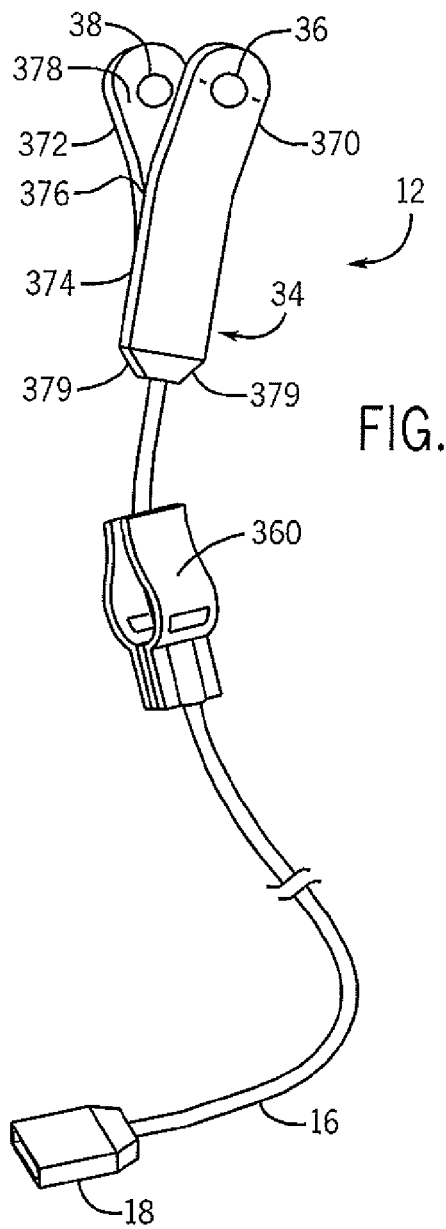
FIG. 19 is a perspective view of the sensor of FIG. 18 in which the sensor is positioned in an open position.
Figure 20:
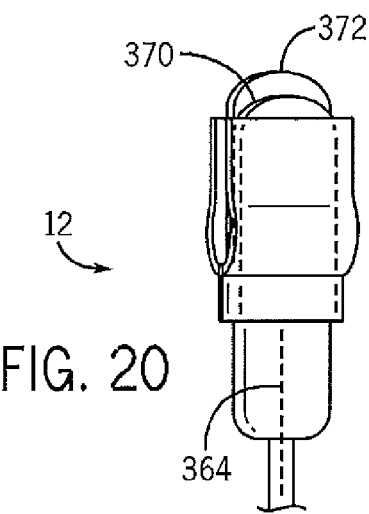
FIG. 20 is a perspective view of the sensor of FIG. 18 in which the sensor is positioned in a closed position.

FIG. 19 is a perspective view of the sensor 12 in which the clip is positioned along the cable 16. The sliding clip 360 is capable of sliding along axis 364 and down the cable 16. The cable terminates in a plug 18. The sensor body 34 is generally Y-shaped and includes a first portion 370 and a second portion 372 that are joined at the stem portion 374 at junction 376 and that are configured to be positioned on opposing side of the earlobe. As depicted, the sensor 12 is in an open configuration, and the first portion 370 and the second portion 372 are not biased towards one another. A foam layer 378 may be positioned on the tissue-contacting side of the first portion 370 and the second portion 372 to provide additional thickness. In another embodiment, a pressure-sensitive adhesive layer may be disposed on the side of the first portion 370 and the second portion 372. The emitter 36 and the detector 38 are disposed on opposing portions. However, it should be understood that the emitter 36 and the detector 38 may be arranged in a reflectance configuration. The sensor body may include features that allow the sliding clip to move easily from the stem portion 374 to the cable 16. As shown, the stein portion 374 includes notches 379 to prevent the sliding clip 360 from catching on the sensor body 34, FIG. 20 shows the sensor in the closed position in which the sliding clip 360 is positioned to bias the first portion 370 and the second portion 372 towards one another. In certain embodiments, the sliding clip 360 is not removable from the sensor 12 by an operator without breaking or tearing the clip 360 or the sensor 12. This may provide the advantage of having an all-in-one sensor assembly without removable parts that may be misplaced. To that end, the clip 360 encircles the sensor 12 in a dimension substantially orthogonal to the axis 364.

Figure 21:
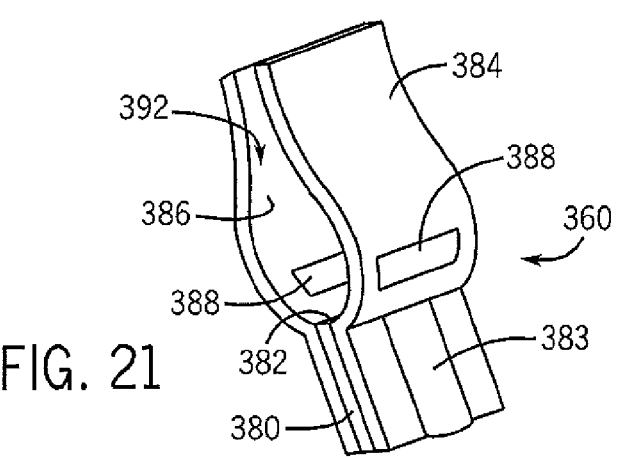
FIG. 21 is a perspective view of a sliding clip.

As shown in FIG. 21 in perspective view, the sliding clip 360 includes an annular base member 380 that defines a passage 382. The passage 382 is large enough to accommodate the cable 16 and the stein portion 374. The base member 380 may include a bump 383 or notch configured to accommodate a slightly thicker cable 16. In addition, the sensor body 34 may include a wider or thicker portion that is larger than the passage 382 and that stops movement of the sliding clip 360 past the stem portion 374. For example, the first portion 370 and the second portion 372 may include an additional layer, such as the foam layer 378, that results in a greater combined thickness of the first and second portions 370 and 372 relative to the stein portion 374. At the other end of the sensor 12, the passage 382 of the sliding clip 360 is smaller than the plug 18.

The sliding clip 360 also includes a first end 384 and a second end 386 that provide the biasing force. The biasing force may be determined by the size and shape of the first end 384 and the second end 386. The first end 384 and the second end 386 may also include cutouts 388 that may adjust the amount of force applied. In certain embodiments, it is contemplated that the sliding clip 360 or other biasing mechanism applies sufficient pressure to the tissue to exceed the typical venous pressure of a patient, but not the diastolic arterial pressure. If the sensor 12 applies a pressure greater than the venous pressure, excess venous blood will be squeezed from the earlobe, thus enhancing the sensitivity of the sensor to variations in the arterial blood signal. In addition, in such an embodiment, the effect of venous pulsations may be dampened. Since the pressure applied by the sensor 12 is designed to be less than the arterial pressure, the application of pressure to the tissue does not interfere with the arterial pulse signal. In certain embodiments, the sensor 12 may be adjusted to overcome venous pressure in the tissue of the ear (e.g., the earlobe), which may be as low as an average pressure of 3-5 mmHg. In certain embodiments, the sensor 12 applies at least enough pressure to overcome about 3-5 mm Hg, about 5 mm Hg, or about 10-15 mm Hg. These pressures may vary because of the location of the vascular bed and the patient's condition. For example, a patient with poor perfusion may have lower venous pressure. It is contemplated that removing venous blood contribution without arterial blood exsanguination may improve the arterial pulse signal. Further, the pressure applied by the sensor 12 may be less than arterial pressure, e.g., the diastolic arterial pressure or the systolic arterial pressure. Typical diastolic arterial pressure and systolic arterial pressures may be about 80 mmHg and 120 mmHg, respectively. However, venous pressure or arterial pressure may be assessed on a patient-by-patient basis.

The sensor 12 may also include alignment features or indicators to facilitate application to the ear. In one embodiment, the sliding clip 360 may slide only to the junction point 376 of the main stem 374 and the first portion 370 and the second portion 372 because the size of the passageway 382 prevents further movement along the axis 364. At that stopping point, the sliding clip 360 is correctly aligned with the sensor body 34 and the emitter 36 and detector 38 to provide the appropriate securing force. In such an embodiment, the correct alignment may be achieved by intuitive feel, which may be advantageous. In other embodiments, the interior surface 392 of the first end 384 and/or the second end 386 may include depressions or protrusions that may mate with complementary features on an exterior surface of the first portion 370 and/or the second portion 372.

The biasing mechanism is depicted as a sliding clip 360. However, the sensor 12 may be secured with a flat spring, a coiled torsion spring, a hinged clip, or other biasing component. Further, in certain embodiments, the biasing mechanism may be removable from the sensor 12. In such embodiments, the sensor 12 may be affixed to the earlobe with a removable flat clip or U-shaped clip that does not encircle the sensor body 34 when applied to the sensor 12. In such embodiments, the sensor body 34 and/or the biasing mechanism may include text or other alignment indicators, for example indicating the position of the emitter 36 and the detector 38, to facilitate proper positioning of the biasing mechanism. The biasing mechanism may be constructed from a variety of materials or combinations of materials that provide the desired resiliency and clamping force. For example, in certain embodiments, the biasing mechanism is constructed from stainless steel. In other embodiments, the biasing mechanism is constructed from polymeric materials, such as acrylonitrile butadiene styrene.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A sensor comprising:
    a sensor body comprising a first portion and a second portion, wherein the first portion and the second portion are configured to be applied to opposing sides of an ear;
    an emitter disposed on the first portion and configured to emit light into a tissue;
    a light detector disposed on the first portion or the second portion and configured to receive the light from the tissue; and
    a moldable member configured to be molded around at least part of the emitter and at least part of the detector and to retain the emitter and the detector at a measurement site when the sensor is applied to the ear, wherein the moldable member is configured to directly contact the tissue and to conform to the tissue when the sensor is applied to the ear.

2. The sensor, as set forth in claim 1, wherein the sensor comprises a release layer disposed on the moldable member such that the moldable member is between the sensor body and the release layer.

3. The sensor, as set forth in claim 1, wherein the moldable member comprises a putty.

4. The sensor, as set forth in claim 1, wherein the moldable member comprises a room temperature vulcanizing silicone.

5. The sensor, as set forth in claim 1, wherein the moldable member is configured to harden or cure when exposed to a particular wavelength of light.

6. The sensor, as set forth in claim 1, wherein the moldable member has a hardness of 20 Shore OO or less.

7. The sensor, as set forth in claim 1, wherein the moldable member is adhesive.

8. The sensor, as set forth in claim 1, wherein the sensor comprises a pulse oximetry sensor.

9. The sensor of claim 1, wherein the moldable member is configured to be removable from the sensor.

10. An ear sensor comprising:
    an electrical connector coupled to an emitter adapted to transmit light into a tissue and a light detector configured to receive the light from the tissue; and
    a moldable member configured to be molded around a portion of the electrical connector such that the moldable member covers at least a portion of the electrical connector and affixes at least a portion of the electrical connector to the tissue when the ear sensor is applied to a patient, and wherein the moldable member is configured to directly contact the tissue when the ear sensor is applied to the patient.

11. The ear sensor, as set forth in claim 10, wherein the moldable member partially surrounds the emitter and the detector.

12. The ear sensor, as set forth in claim 10, wherein the moldable member comprises a dental impression material.

13. The ear sensor, as set forth in claim 10, wherein the sensor comprises a backing layer disposed on a surface of the moldable material.

14. The ear sensor, as set forth in claim 10, wherein the electrical connector comprises a flexible circuit and wherein the moldable material is disposed on a non-tissue contacting side of the flexible circuit.

15. A method comprising:
    applying an emitter adapted to transmit light into a patient's tissue and a light detector configured to receive the transmitted light from the tissue onto an ear; and
    molding a putty over and around the emitter and the detector to affix the emitter and the detector onto the ear, wherein the putty is configured to directly contact the patient's tissue when applied to the ear.

16. The method of claim 15, comprising molding the putty around at least a portion of an electrical connector coupled to the emitter and the detector to affix the portion of the electrical connector to the ear.

17. The method of claim 15, wherein molding the putty around the emitter and the detector comprises molding the putty around an earlobe.

18. The method of claim 15, wherein molding the putty around the emitter and the detector comprises molding the putty around a helix of the ear.

19. The method of claim 15, comprising exposing the putty to a temperature at which the putty is configured to harden.

20. The method of claim 15, comprising exposing the putty to a predetermined wavelength of light configured to harden the putty.

* * * * *